(12) United States Patent
Stefan

(10) Patent No.: US 12,310,653 B2
(45) Date of Patent: May 27, 2025

(54) HIGH-FREQUENCY (HF) MEDICAL INSTRUMENT

(71) Applicant: KARL STORZ SE & Co. KG, Tuttlingen (DE)

(72) Inventor: Jochen Stefan, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 482 days.

(21) Appl. No.: 17/966,781

(22) Filed: Oct. 15, 2022

(65) Prior Publication Data

US 2023/0123852 A1    Apr. 20, 2023

(51) Int. Cl.
*A61B 18/14* (2006.01)
*A61B 17/00* (2006.01)
*A61B 18/00* (2006.01)

(52) U.S. Cl.
CPC ...... *A61B 18/1492* (2013.01); *A61B 2017/00314* (2013.01); *A61B 2018/00184* (2013.01)

(58) Field of Classification Search
CPC ...... A61B 18/1492; A61B 2017/00314; A61B 2018/00184
See application file for complete search history.

(56) References Cited

U.S. PATENT DOCUMENTS

2016/0128766 A1* 5/2016 Hyodo ............... A61B 34/30
606/41

FOREIGN PATENT DOCUMENTS

DE    10 2012 100 604    4/2012
WO         9743942       11/1997
WO    WO-2011156340 A2 * 12/2011 ............. A61B 17/00

OTHER PUBLICATIONS

Jul. 19, 2022—(DE) Examination Report—App. No. 10 2021 126 896.6.

* cited by examiner

*Primary Examiner* — Linda C Dvorak
*Assistant Examiner* — Abigail Bock
(74) *Attorney, Agent, or Firm* — Banner & Witcoff, Ltd.

(57) ABSTRACT

The invention relates to a medical instrument having a hollow shaft, whose proximal end can be connected to an operating unit and having a tool tip arranged at the distal end of the shaft having a tool arranged at the distal end of the tool tip, wherein the tool has two jaw parts, which can be pivoted relative to one another and wherein the jaw parts are pivoted via actuating elements, which are mounted so as to be axially displaceable in the shaft and which can be actuated on the proximal side via the operating unit and wherein the tool tip can be pivoted via a joint mechanism relative to the longitudinal axis of the shaft.

Figure 1:
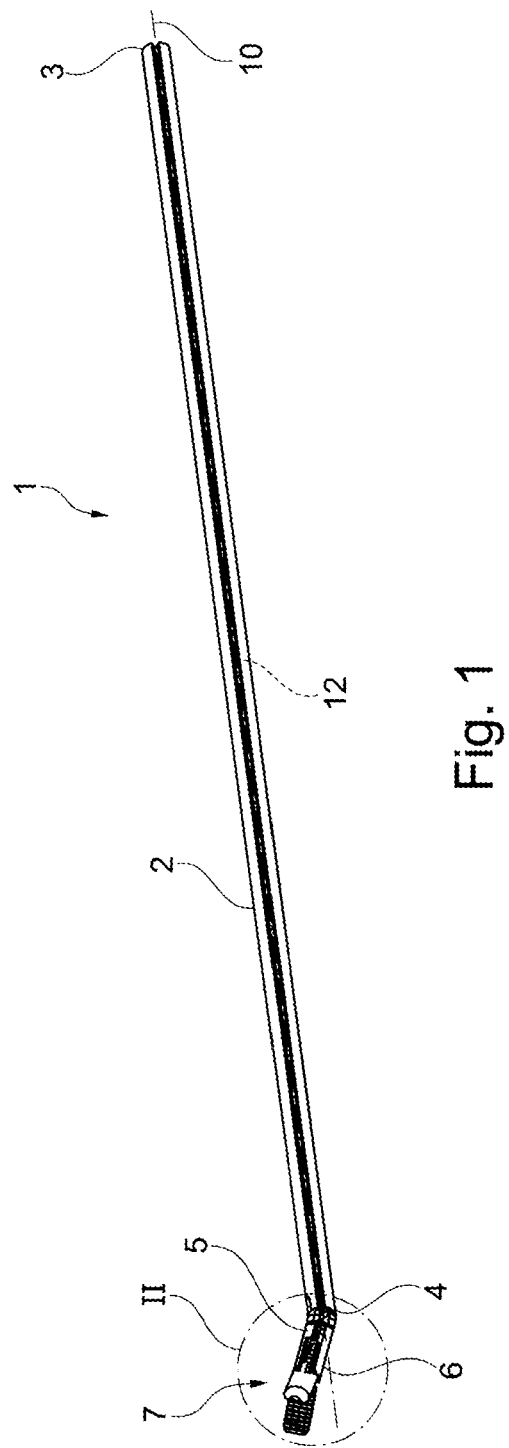

In order to provide a medical instrument, which ensures a uniform transmission of tensile and compressive forces even via the pivot region to the tool tip, it is proposed according to the invention that the pivotable jaw parts are each coupled via an articulated drive element to the distal end of an actuating element mounted so as to be axially displaceable in the shaft such that the articulated drive element spans the region of the joint mechanism between the distal end of the shaft and the proximal end of the tool tip.

6 Claims, 2 Drawing Sheets

HIGH-FREQUENCY (HF) MEDICAL INSTRUMENT

This application claims the benefit of and priority to DE 10 2021 126 896.6, entitled "HIGH-FREQUENCY (HF) MEDICAL INSTRUMENT" filed Oct. 16, 2021, which is hereby incorporated by reference in its entirety for any and all non-limiting purposes.

The invention relates to a high-frequency (HF) medical instrument having a hollow shaft, whose proximal end can be connected to an operating unit and having a tool tip arranged at the distal end of the shaft having a tool arranged at the distal end of the tool tip, which is arranged at the distal end of the shaft and which can be pivoted via a joint mechanism relative to the longitudinal axis of the shaft and having a HF tool arranged at the distal end of the tool tip, wherein the power supply to the HF tool takes place via an inner cable.

Medical instruments for endoscopic surgery generally have a hollow shaft, at whose proximal end is arranged a handle or operating unit and at whose distal end is arranged a tool consisting of two jaw parts movable relative to one another. In the case of robotic surgery, the operating unit can also be located outside of the OP. In order to be able to cover an effective region that is as large as possible using the tool under the often restrictive working conditions, many endoscopic instruments are designed such that, in addition to the mere actuation of the tool, a tool tip bearing the tool is designed to be bendable with respect to the longitudinal axis of the shaft. In practice, medical instruments of this type are used as hand-operated instruments and also as instruments for a medical telemanipulated robot.

A generic medical instrument is also known from WO 97/43942 A1. In order to be able to actuate the jaw parts at all times even with an angled tool tip, the force is transmitted to the jaw parts via cable strands in this known medical instrument. The use of the cable strands has the advantage that the pivot region between the rigid proximal shaft and the pivotable distal tool tip can be spanned well using cable strands, but the tensile strength of the cable strands is limited and due to the tensile and bending forces occurring in the pivot region, their lifespan is limited. Moreover, virtually no compressive forces can be transmitted via cable strands and the cleaning of cable strands is also very difficult in practice.

In the case of the design of the medical instrument as a HF instrument designed with a pivotable tool tip, in particular the region of the joint mechanism presents a problem since the cable for the power supply to the HF tool has to be guided coming from the hollow shaft in a bend-free manner towards the pivotable tool tip.

Based on this, the object underlying the invention is to provide a HF medical instrument of the type mentioned at the outset, which ensures damage-free guidance of the power cable for the HF tool even via the pivot region to the tool tip.

The solution to this object is characterized according to the invention in that in the region of the joint mechanism between the distal end of the shaft and the proximal end of the tool tip is arranged a multi-link joint element spanning the joint mechanism, wherein the cable is mounted in the region of the joint mechanism so as to be guided on the multi-link joint element.

The multi-link joint element arranged in the region of the joint mechanism enables any angling of the tool tip relative to the longitudinal axis of the shaft to be followed without the occurrence of sharp bends, due to its multi-link articulated structure. By mounting the cable so as to be guided on this multi-link joint element, bending stress of the cable is also prevented.

For the design of the multi-link joint element, it is proposed according to a practical embodiment of the invention that the multi-link joint element is designed as a roller chain consisting of a plurality of chain links. The use of a roller chain has the advantage that a roller chain is a low-maintenance and long-life component, which enables bend-free guidance of the cable mounted on the roller chain in the case of sufficient articulation in the pivot region to the tool tip.

The chain links of the roller chains are according to the invention structured such that each chain link of the roller chain consists of two outer tabs spaced apart from one another, and two pins connecting the outer tabs to one another, wherein two chain links can be connected to one another via an intermediate tab, which is mounted on in each case one pin of the two chain links and is arranged between the two outer tabs of the two chain links and wherein all pins protrude outwards over one of the outer tabs at least in the direction of the outer side of the shaft or the outer side of the tool tip forming an overhang on one side and in these overhangs of the pins are designed through-boreholes running transversely to the longitudinal direction of the pins for receiving the cable.

The mounting of the cable in the through-boreholes of the pins ensures that, on the one hand, the cable does not enter between the individual chain links of the roller chain and, on the other hand, there is always parallel guidance of the cable relative to the roller chain, whereby the bend-free guidance of the cable is also ensured in the axial direction.

In order to prevent tensile loads occurring on the cable when pivoting the individual chain links of the multi-link joint element or the roller chain, it is proposed according to the invention that the inner diameter of the through-boreholes is greater than the outer diameter of the cable, whereby a relative movement of the individual chain links in relation to the cable mounted in the through-boreholes is enabled.

With a practical embodiment of the invention, it is also proposed that the multi-link joint element is designed as part of an axially-displaceable drive for the HF tool. For the design of a drive for the distal-side HF instrument, the use of a multi-link joint element in the region of the joint mechanism is also advantageous since the multi-link joint element enables a play-free force transmission of the axial tensile and compressive forces independently of the pivot position of the tool tip relative to the longitudinal axis of the shaft.

Lastly, it is proposed with the invention that the roller chain is mounted in the region of the joint mechanism between the distal end of the shaft and the proximal end of the tool tip so as to be guided via a chain wheel pair consisting of two chain wheels. The chain wheels serve to guide the roller chain in the region of the joint mechanism.

Figure 2:
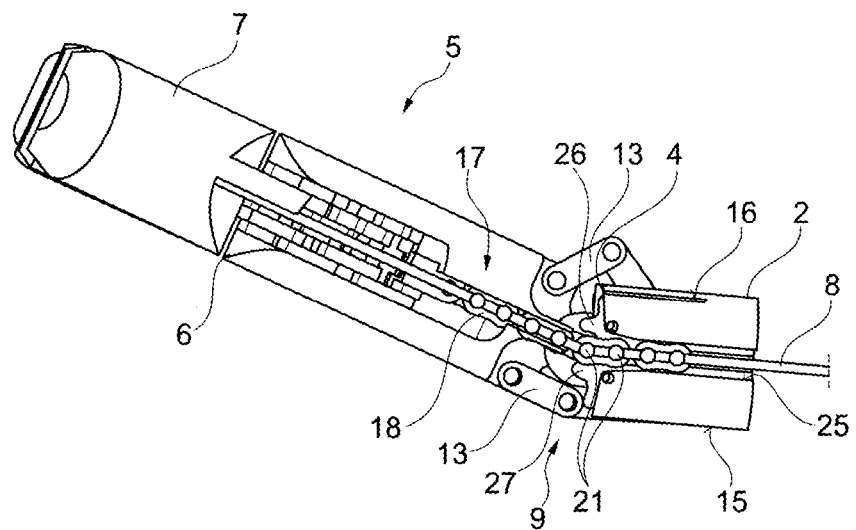

Further features and advantages of the invention will emerge on the basis of the associated drawings, in which an exemplary embodiment of a medical instrument according to the invention is illustrated only by way of example without the invention being limited to this exemplary embodiment. The drawings show:

FIG. 1 a perspective view of a medical instrument according to the invention;

FIG. 2 an enlarged view of the detail II according to FIG. 1 and

Figure 3:
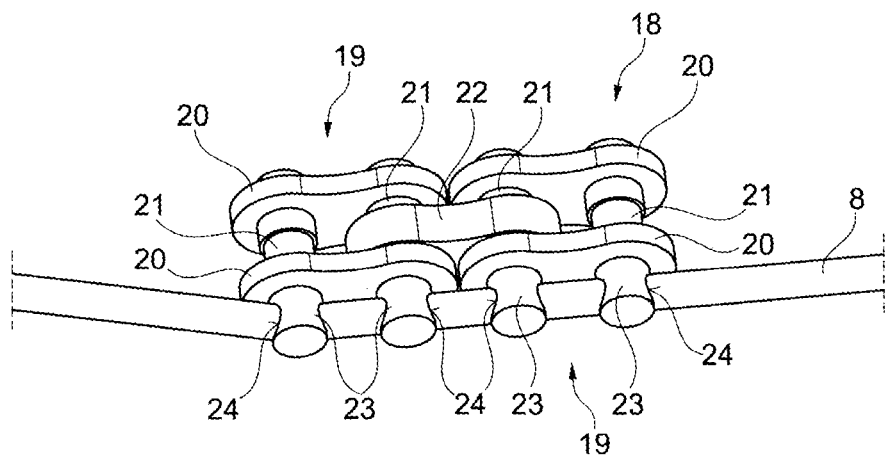

FIG. 3 an enlarged perspective top view of two chain links of the roller chain connected to one another according to FIG. 2.

The image of FIG. 1 shows a HF medical instrument 1 with a hollow shaft 2, whose proximal end 3 can be connected to an operating unit not illustrated and with a tool tip 5 arranged at the distal end 4 of the shaft 2. The operating unit can be a manually-actuated handle or even the control unit of a medical telemanipulated robot.

At the distal end 6 of the tool tip 5 is arranged a HF tool 7. The power supply to the HF tool 7 takes place via a cable 8, which runs from proximal to distal inside the outer diameter of the shaft 2 and of the tool tip 5.

To increase the degrees of freedom of the HF medical instrument 1, the tool tip 5 bearing the HF tool 7 can be pivoted upwards and downwards by up to 90° relative to the longitudinal axis 10 of the shaft 2 about the pivot point 11 via a joint mechanism 9.

The tool tip 5 is pivoted via two actuating elements 12, which are mounted so as to be axially displaceable in the shaft 2 and which can be actuated on the proximal side via the operating unit. By means of the tool tip 5, the distal ends of the two actuating elements 12 are connected via in each case one link chain 13, which consists of a plurality of chain links and which is in each case mounted, on the one hand, at the distal end of the associated actuating element 12 and, on the other hand, at the proximal end 14 of the tool tip 5.

In order to receive and mount in a guided manner the two link chains 13 of the joint mechanism 9 to pivot the tool tip 5 in the region of the shaft 2, in the outer surface 15 of the distal end 4 of the shaft 2 are designed grooves 16 open outwards and offset by 180° in relation to one another for receiving in a guided manner the link chains 13.

The use of the link chains 13 as drive elements for pivoting the tool tip 5 is advantageous precisely in the transition region from the distal end 4 of the shaft 2 to the proximal end 14 of the tool tip 5 since the individual chain links of the individual link chains 13 ensure a uniform movement due to their mutual articulated mounting on one another and they ensure the transmission of both compressive forces and tensile forces.

In order to ensure that the cable 8 serving as the power supply to the HF tool 7 is not exposed to any bending stress when pivoting the tool tip 5 in the region of the joint mechanism 9, a multi-link joint element 17 spanning the joint mechanism 9 is arranged in the region of the joint mechanism 9 between the distal end 4 of the shaft 2 and the proximal end 14 of the tool tip 5, wherein the cable 8 is mounted in the region of the joint mechanism 9 so as to be guided on the multi-link joint element 17.

The multi-link joint element 17 designed in the embodiment according to FIG. 2 as a roller chain 18 enables any angling of the tool tip 5 relative to the longitudinal axis 10 of the shaft 2 to be followed without sharp bends occurring, due to its multi-link articulated structure. By mounting the cable 8 so as to be guided on this multi-link joint element 17 or the roller chain 18, bending stress of the cable 8 is also prevented.

FIG. 3 shows two chain links 19 of the roller chain 18. Each chain link 19 consists of two outer tabs 20 spaced apart from one another and two pins 21 connecting the outer tabs 20 to one another. In order to form a multi-link roller chain 19, two chain links 19 arranged behind one another are connected to one another via an intermediate tab 22, which is mounted on in each case one pin 21 of the two chain links 19 and is arranged between the outer tabs 20 of the two chain links 19 connected to one another.

As is also discernible from FIG. 3, all pins 21 of the chain links 19 protrude outwards over one of the outer tabs 20 on one side at least in the direction of the outer side of the shaft 2 or the outer side of the tool tip 5 forming an overhang 23. In order to mount the cable 8 so as to be guided on the roller chain 18, through-boreholes 24 running transversely to the longitudinal direction of the pins 21 for receiving the cable 8 are designed in the overhangs 23 of the pins 21.

The mounting of the cable 8 in the through-boreholes 24 of the pins 21 ensures that, on the one hand, the cable 8 does not enter between the individual chain links 19 of the roller chain 18 and, on the other hand, there is always parallel guidance of the cable 8 relative to the roller chain 18, whereby the bend-free guidance of the cable 8 is also ensured in the axial direction.

In order to prevent tensile loads occurring on the cable 8 when pivoting the individual chain links 19 of the multi-link joint element 17 or the roller chain 18, the inner diameter of the through-boreholes 24 is greater than the outer diameter of the cable 8, whereby a relative movement of the individual chain links 19 in relation to the cable 8 mounted in the through-boreholes 24 is enabled and the occurrence of tensile loads on the cable 8 is prevented.

The multi-link joint element 17 or the roller chain 18 is mounted in the region of the shaft 2 so as to be guided via a groove 25 open outwards and designed in the outer surface 15 of the distal end 4 of the shaft 2, as can be inferred in particular from the image of FIG. 2.

The grooves 16 for receiving in a guided manner the link chains 13 for pivoting the tool tip 5 and the groove 25 for receiving in a guided manner the multi-link joint element 17 or the roller chain 18 are arranged offset by 90° in relation to one another in the outer surface 15 of the distal end 4 of the shaft 2.

In the case of the embodiment of the HF medical instrument illustrated in FIG. 2, the distal-side HF tool 7 is designed as an adjustable HF tool 7, which can be actuated via an axially-displaceable drive by means of the proximal operating unit. In the case of this embodiment of the HF tool 7, the multi-link joint element 17 or the roller chain 18 forms a part of this axially-displaceable drive for the adjustable HF tool 7.

In the region of the joint mechanism 9 between the distal end 5 of the shaft 2 and the proximal end 14 of the tool tip 5 is mounted the roller chain 18 so as to be guided via a chain wheel pair consisting of two chain wheels 26 and 27, wherein the chain wheels 26 and 27 of the n chain wheel pair are arranged in relation to one another such that a chain wheel 26 from above and a chain wheel 27 from below engage at the same chain link 19 of the roller chain 18. By arranging the two chain wheels 26 and 27 of the chain wheel pair in different planes relative to the roller chain 18, it is possible to guide and support the roller chain 18 in the region of the joint mechanism 9.

A HF medical instrument 1 designed as previously described is characterized in that, regardless of the angle position of the tool tip 5 relative to the longitudinal axis 12 of the shaft 2, damage-free guidance of the power-conducting cable 8 for the HF tool 7 is ensured via the pivot region from the shaft 2 to the tool tip 5.

LIST OF REFERENCE NUMERALS

1 HF medical instrument
2 Shaft
3 Proximal end (shaft)
4 Distal end (shaft)

5 Tool tip
6 Distal end (tool tip)
7 HF tool
8 Cable
9 Joint mechanism
10 Longitudinal axis (shaft)
11 Pivot point
12 Actuating element
13 Link chain
14 Proximal end (tool tip)
15 Outer surface (shaft)
16 Groove
17 Multi-link joint element
18 Roller chain
19 Chain link
20 Outer tab
21 Pin
22 Intermediate tab
23 Overhang
24 Through-borehole
25 Groove
26 Chain wheel
27 Chain wheel

The invention claimed is:

1. A high-frequency (HF) medical instrument having a hollow shaft, whose proximal end can be connected to an operating unit and having a tool tip, which is arranged on the distal end of the shaft and which can be pivoted via a joint mechanism relative to the longitudinal axis of the shaft and having a HF tool arranged on the distal end of the tool tip, wherein the power supply to the HF tool takes place via an inner cable,
characterized in
that in the region of the joint mechanism between the distal end of the shaft and the proximal end of the tool tip is arranged a multi-link joint element spanning the joint mechanism, wherein the cable is mounted in the region of the joint mechanism so as to be guided on the multi-link joint element.

2. The HF medical instrument according to claim 1, characterized in that the multi-link joint element is designed as a roller chain consisting of a plurality of chain links.

3. The HF medical instrument according to claim 1, characterized in that each chain link of the roller chain consists of two outer tabs spaced apart from one another and two pins connecting the outer tabs to one another, wherein two chain links can be connected to one another via an intermediate tab, which is mounted on in each case one pin of the two chain links and is arranged between the two outer tabs of the two chain links, wherein all pins protrude outwards over one of the outer tabs on one side at least in the direction of the outer side of the shaft or the outer side of the tool tip forming an overhang and in these overhangs of the pins are designed through-boreholes running transversely to the longitudinal direction of the pins for receiving the cable.

4. The HF medical instrument according to claim 3, characterized in that the inner diameter of the through-boreholes is greater than the outer diameter of the cable.

5. The HF medical instrument according to one of claim 1, characterized in that the multi-link joint element is designed as part of an axially-displaceable drive for the HF tool.

6. The HF medical instrument according to one of claim 2, characterized in that the roller chain is mounted in the region of the joint mechanism between the distal end of the shaft and the proximal end of the tool tip so as to be guided via a chain wheel pair consisting of two chain wheels.

\* \* \* \* \*